US009001957B2

(12) United States Patent
Cabrera et al.

(10) Patent No.: US 9,001,957 B2
(45) Date of Patent: Apr. 7, 2015

(54) CHEMISTRY PROBE ASSEMBLIES AND METHODS OF USING THE SAME IN NUCLEAR REACTORS

(75) Inventors: Filemon Tecson Cabrera, Wilmington, NC (US); Angelito Foz Gonzaga, San Jose, CA (US); Edgardo V. Nazareno, Morgan Hill, CA (US); Russell Seeman, San Jose, CA (US); Samson Hettiarachchi, Menlo Park, CA (US)

(73) Assignee: GE-Hitachi Nuclear Energy Americas LLC, Wilmington, NC (US)

( * ) Notice: Subject to any disclaimer, the term of this patent is extended or adjusted under 35 U.S.C. 154(b) by 969 days.

(21) Appl. No.: 12/968,898

(22) Filed: Dec. 15, 2010

(65) Prior Publication Data

US 2012/0155595 A1 Jun. 21, 2012

(51) Int. Cl.
*G21C 17/00* (2006.01)
*G21C 17/022* (2006.01)
*G01N 17/04* (2006.01)

(52) U.S. Cl.
CPC .............. *G21C 17/022* (2013.01); *G01N 17/04* (2013.01)

(58) Field of Classification Search
USPC .................................................. 376/245, 249
See application file for complete search history.

(56) References Cited

U.S. PATENT DOCUMENTS

| | | | | | |
|---|---|---|---|---|---|
| 3,639,876 | A | * | 2/1972 | Wilson | 338/13 |
| 4,667,150 | A | * | 5/1987 | Hausler et al. | 324/700 |
| 4,784,729 | A | * | 11/1988 | Jasinski | 205/775.5 |
| 5,192,414 | A | * | 3/1993 | Indig et al. | 204/400 |
| 5,465,278 | A | * | 11/1995 | Cowan et al. | 376/245 |
| 6,181,760 | B1 | * | 1/2001 | JinKim | 376/245 |
| 6,222,307 | B1 | | 4/2001 | Roy et al. | |
| 6,623,611 | B1 | | 9/2003 | Jett et al. | |

FOREIGN PATENT DOCUMENTS

| | | |
|---|---|---|
| JP | 59133494 A | 7/1984 |
| JP | 02280042 A | 11/1990 |
| JP | 03100451 A | 4/1991 |
| JP | 03218452 A | 9/1991 |
| JP | 05188178 A | 7/1993 |
| JP | 08068888 A | 3/1996 |
| JP | 2009025021 A | 2/2009 |

OTHER PUBLICATIONS

JP Notice of Reasons for Refusal issued in connection with corresponding JP Patent Application No. 2011-268580 dated on Oct. 25, 2013.

* cited by examiner

Primary Examiner — Timothy A Brainard
(74) Attorney, Agent, or Firm — Harness, Dickey & Pierce, P.L.C.

(57) ABSTRACT

Electrochemical corrosion potential (ECP) probe assemblies may be used to monitor ECP of materials due to coolant chemistry in an operating nuclear reactor. Example embodiment assemblies include at least one ECP probe that detects ECP of potentially several different materials, a structural body providing a fluid flow path for the coolant over the ECP probes, and a signal transmitter that transmits or carries ECP data to an external receiver. The ECP probes may be of any number and/or type, so as to detect ECP for different component materials, including stainless steel, a zirconium alloys, etc. The ECP probes may further detect ECP due to ion concentration, pH, etc. The ECP data may be transmitted through wired or wireless signal transmitters. Example methods include installing and using example embodiment ECP probe assemblies in nuclear reactors and facilities.

19 Claims, 6 Drawing Sheets

CHEMISTRY PROBE ASSEMBLIES AND METHODS OF USING THE SAME IN NUCLEAR REACTORS

BACKGROUND

Figure 1:
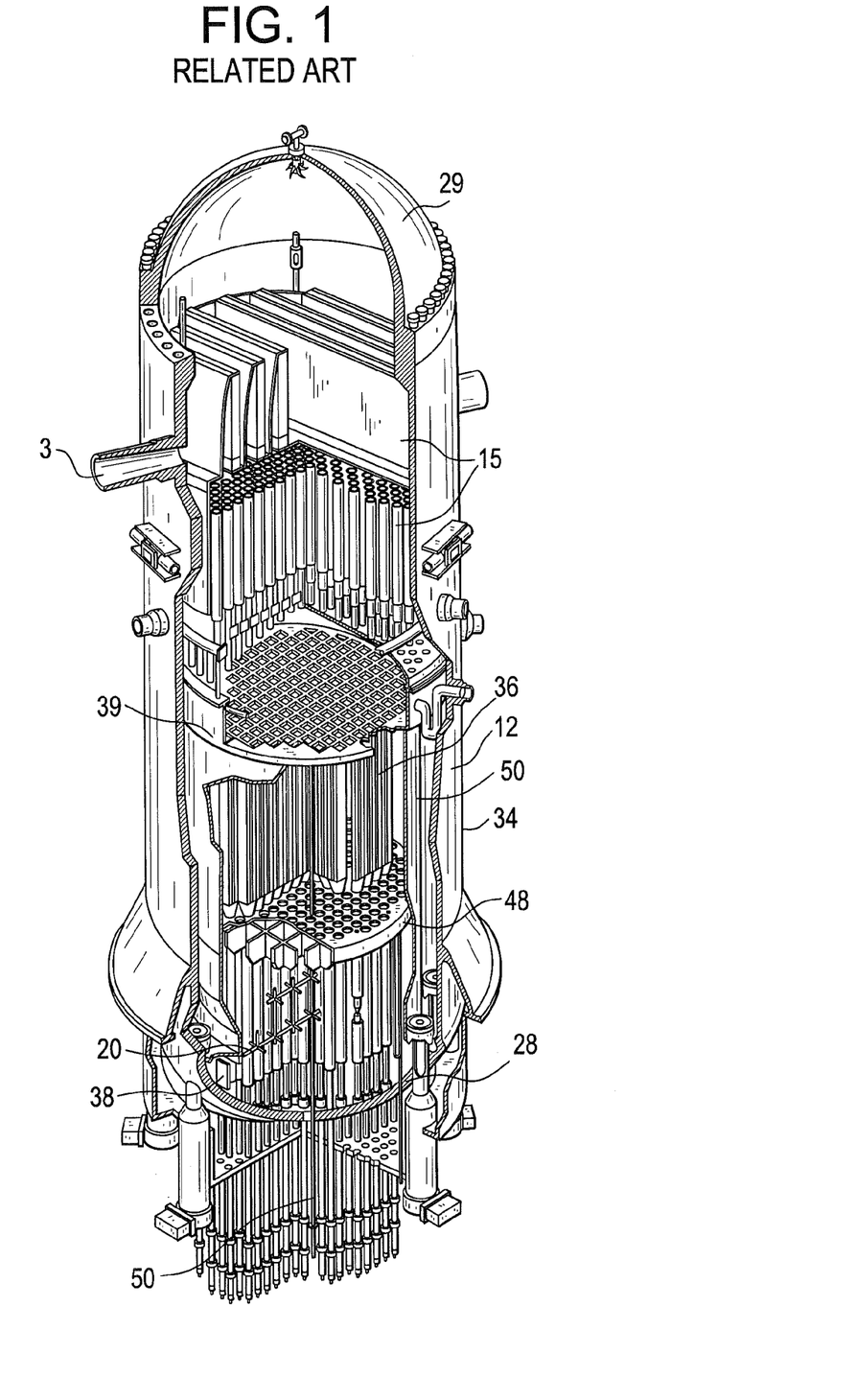
FIG. 1 is an illustration of a conventional Reactor Pressure Vessel and internals.

As shown in FIG. 1, a conventional nuclear reactor, such as a Boiling Water Reactor (BWR), may include a reactor pressure vessel (RPV) 12 with a generally cylindrical shape. RPV 12 may be closed at a lower end by a bottom head 28 and at a top end by a removable top head 29. A cylindrically-shaped core shroud 34 may surround reactor core 36, which includes several nuclear fuel elements that generate power through fission. Shroud 34 may be supported at one end by a shroud support 38 and may include a removable shroud head 39 and separator tube assembly at the other end. Fuel bundles may be aligned by a core plate 48 located at the base of core 36. One or more control blades 20 may extend upwards into core 36, so as to control the fission chain reaction within fuel elements of core 36. Additionally, one or more instrumentation tubes 50 may extend into reactor core 36 from outside RPV 12, such as through bottom head 28, permitting instrumentation, such as neutron monitors and the thermocouples, to be inserted into and enclosed within the core 36 from an external position.

A fluid coolant, such as water, is circulated up through core 36 and core plate 48 and is at least partially converted to steam by the heat generated by fission in the fuel elements. The steam is separated and dried in separator tube assembly and steam dryer structures 15 and exits RPV 12 through a main steam nozzle 3 near top of RPV 12. The coolant circulated through and boiled in RPV 12 is typically pure and deionized, except for some additives that enhance coolant chemistry. While attempts are made to maintain a stable coolant chemistry that is inert with respect to components and fuel in RPV 12, coolant chemistry may be adjusted to meet operational needs or changed through component failure. For example, a soluble neutron absorber may be added to the coolant to better control the nuclear reaction in core 36, or fission products may be inadvertently leaked into the coolant through failure of fuel elements in core 36, or hydrogen may be produced in fuel elements through high-temperature cladding-coolant reactions.

Conventionally, coolant chemistry is monitored through several mechanisms in order to understand coolant chemistry impact on the reactor internals discussed above and to successfully adjust coolant chemistry to meet operational needs. For example, electrochemical corrosion potential (ECP), a property of materials used in the reactor that reflects corrosion and cracking of the material in various coolant conditions, may be monitored by ECP probes in contact with circulating coolant. Access to RPV 12 is limited and difficult during operation and coolant circulation, such that only specific positions may be available for ECP monitoring. ECP probes may be placed in various positions in instrumentation tubes 50 and, through sampling holes in instrumentation tubes, contact circulating coolant to measure component ECP. Other ECP probes may be placed in a bottom head 28 drain line (not shown) or in other coolant piping to sample coolant chemistry for component ECP. For example, ECP probes may be placed in a Mitigation Monitoring System manifold or Recirculation Piping System and contact coolant flowing therein to measure component ECP. Similarly, coolant may be extracted from a coolant loop servicing RPV 12 and raised to reactor-level conditions in a laboratory autoclave, in order to sample ECP with an ECP probe outside RPV 12.

SUMMARY

Example embodiments are directed to electrochemical corrosion potential (ECP) probe assemblies that may be used to monitor component ECP properties resulting from coolant chemistry in an operating nuclear reactor. Example embodiment assemblies include at least one ECP probe that detects component ECP for potentially several different reactor materials, a structural body providing a fluid flow path for the coolant over the ECP probes, and a signal transmitter that transmits or carries ECP data detected by the ECP probes to an external receiver. The ECP probes may be of any number and/or type, so as to detect ECP for different component materials, including stainless steel, a zirconium alloys, etc, exposed to reactor coolant. The ECP probes may further detect coolant chemistry including ion concentration, pH, etc. that measures corrosion or cracking potential of materials exposed to the coolant. The ECP probes may be housed in the structural body in the fluid flow path such that coolant contact and ECP detection is maximized. The ECP probe assembly may include a venturi or other structure at the coolant inlet to enhance fluid flow and ECP detection. The ECP data may be transmitted through wired or wireless signal transmitters to the external receiver so that material health within the operating nuclear reactor may be assessed without accessing the reactor internals.

Example methods include installing and using example embodiment ECP probe assemblies in nuclear reactors and facilities. Example methods include securing the ECP probe assembly in a desired location in the facility and communicatively connecting the ECP probe to the receiver that may receive and/or process the ECP data for operating the facility based on the same. The installation location may be determined based on components in the facility in proximity to the desired location and/or anticipated fluid conditions at the desired location. For example, ECP probe assemblies may be installed on a core shroud wall 34, or at a top of the core in the reactor pressure vessel 12, where coolant chemistry has a large impact on reactor operation but has previously been unobtainable. The ECP probe assembly may include extensions that permit the assembly to be affixed to a nearby structure at the desired location through the extensions. Example methods may position the ECP probe assembly so that the fluid flows through the ECP probe assembly. Example methods may further connect a communications conduit between the ECP and an instrumentation tube in a nuclear reactor by running the conduit down a core shroud wall 34 to a core plate 48 and across the core plate 48 to the instrumentation tube 50.

DETAILED DESCRIPTION

Hereinafter, example embodiments will be described in detail with reference to the attached drawings. However, specific structural and functional details disclosed herein are merely representative for purposes of describing example embodiments. The example embodiments may be embodied in many alternate forms and should not be construed as limited to only example embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected," "coupled," "mated," "attached," or "fixed" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

As used herein, the singular forms "a," "an," and "the" are intended to include the plural forms as well, unless the language explicitly indicates otherwise. It will be further understood that the terms "comprises", "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures or described in the specification. For example, two figures or steps shown in succession may in fact be executed in parallel and concurrently or may sometimes be executed in the reverse order or repetitively, depending upon the functionality/acts involved.

The inventors of the present application have identified several previously-unrecognized problems with conventional electrochemical corrosion potential (ECP) monitoring devices and methods. For example, gathering and transmitting ECP data for materials in reactor coolant in multiple positions within a reactor pressure vessel may not be possible due to limited access to reactor pressure vessels during operation. Coolant accessible to ECP probes in instrumentation tubes may have different chemistry, temperature, pressure, etc., resulting in different material ECP characteristics, from materials at other important reactor pressure vessel locations, such as within the reactor core, near shroud weldings, below a steam dryer, etc. Moreover, radiation levels near these different locations may vary and have greater impact on material ECP than near just the instrumentation tubes. As such, it may be difficult to accurately determine how radiation and coolant affects other reactor pressure vessel internals that are subject to ECP damage from coolant chemistry. Further, placement of ECP probes in multiple instrumentation tubes may limit space available for other types of instrumentation within the tubes and/or increase the likelihood of coolant leakage into such tubes. Example embodiments and methods discussed below uniquely address these previously-unidentified effects of conventional ECP monitoring to achieve several advantages, including improved material ECP monitoring at several positions within a nuclear reactor, improved reactor coolant chemistry control, reduced usage of instrumentation tube space, and/or other advantages discussed below or not, in nuclear power plants.

Example Embodiments

Figure 2:
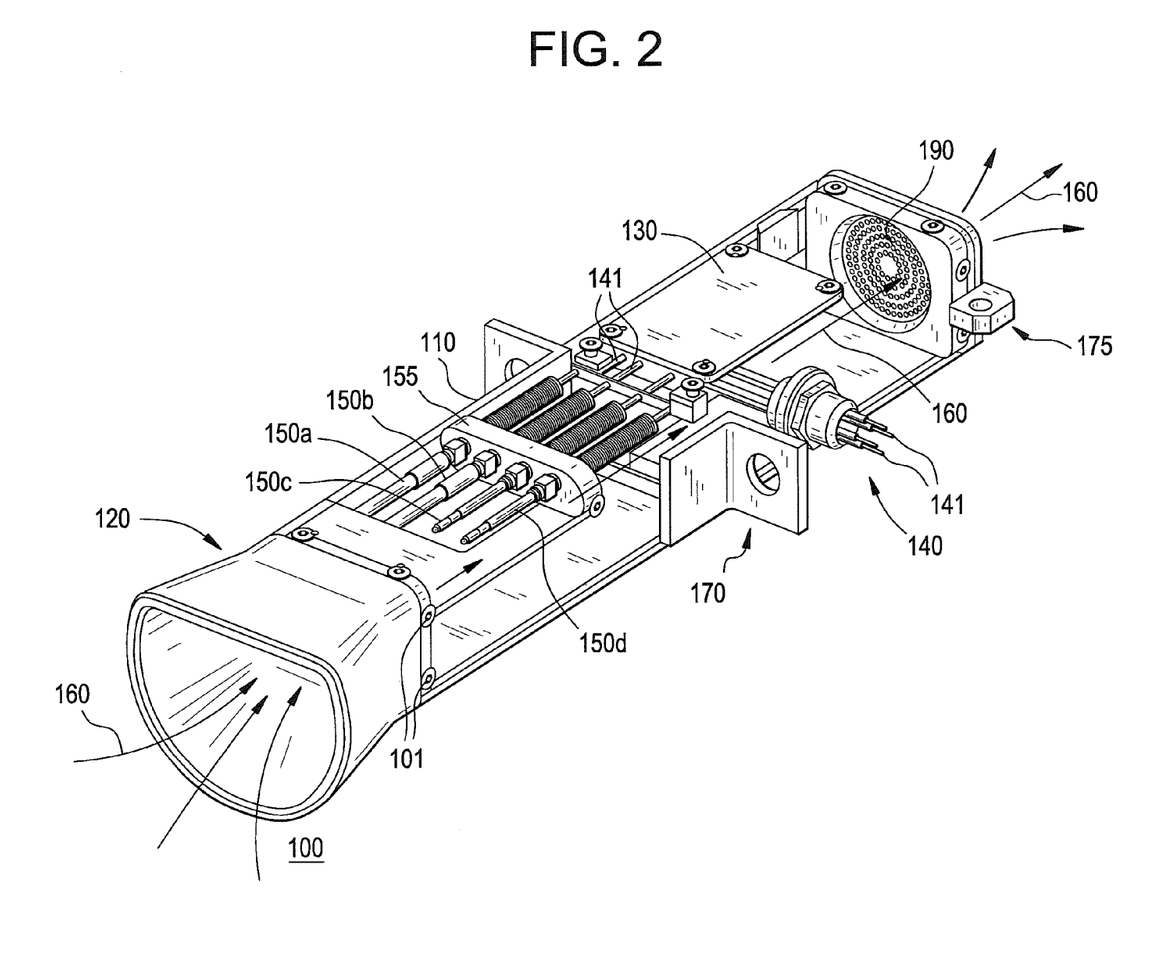
FIG. 2 is an illustration of an example embodiment ECP Probe Assembly.

FIG. 2 is an illustration of an example embodiment ECP probe assembly 100. As shown in FIG. 2, ECP probe assembly 100 includes at least one ECP probe 150. For example, ECP probe assembly may include four ECP probes 150a, 150b, 150c, 150d, or any other desired number of probes. ECP probes 150 may be known types of ECP probes. For example, U.S. Pat. No. 5,192,414, incorporated herein in its entirety by reference, discloses an ECP probe with a stainless steel electrode for measuring ECP of stainless steel in coolant. The ECP of, and thus damage potential for, stainless steel components may be measured by a voltage generated in the stainless steel electrode when contacted with coolant. Or, for example, U.S. Pat. Nos. 6,222,307 and 6,623,611, both incorporated herein in their entirety by reference, disclose other types of ECP probes with platinum and/or zirconium alloy tips that measure ECP for other materials, such as zircaloys, based on coolant properties such as pH levels.

ECP probes 150a, b, c, d may be of a same or different types. For example, ECP probe 150a and 150d may measure ECP with regard to stainless steel, while ECP probe 150c may measure ECP with regard to Inconel, while ECP probe 150b may yet further measure ECP with regard to zircaloy. Any number and combination of types of ECP probes 150 may be used in example embodiment ECP probe assembly 100, based on types of materials used in a subject reactor, based on types of component materials closest to example embodiments installed in nuclear reactors, and/or based on particular anticipated types of coolant chemistry, for example. For example, ECP probes 150c and 150d may be ceramic ball-shaped probes having iron ferrite sensor particles clustered within the ceramic ball-shaped structure, and ECP probes 150a and 150b may be platinum-type sensors having platinum particles in cylindrical probes positioned similarly as the ceramic ball-shaped probes, 150d and 150c.

ECP probes 150a, 150b, 150c, and 150d are mounted in example embodiment ECP probe assembly 100 so as to come into contact with coolant fluid flow 160 through example embodiment ECP probe assembly 100, such as during reactor operation. For example, ECP probes 150a, 150b, 150c, and 150d may be mounted in an alignment housing 155 such that active electrodes at an end of ECP probes 150a, 150b, 150c, and 150d are facing into coolant fluid flow 160. Alternately, one or more ECP probes 150 may be at an angle or perpendicular to coolant fluid flow 160. Alignment housing 155 may rigidly align ECP probes 150 within structural body 110 of example embodiment ECP probe assembly 100. For example, alignment housing 155 may be welded or otherwise affixed to structural body 110 with, for example, fasteners 101, which may be flat head screws, pins, tangs, magnets, adhesives, etc.

Figure 4:
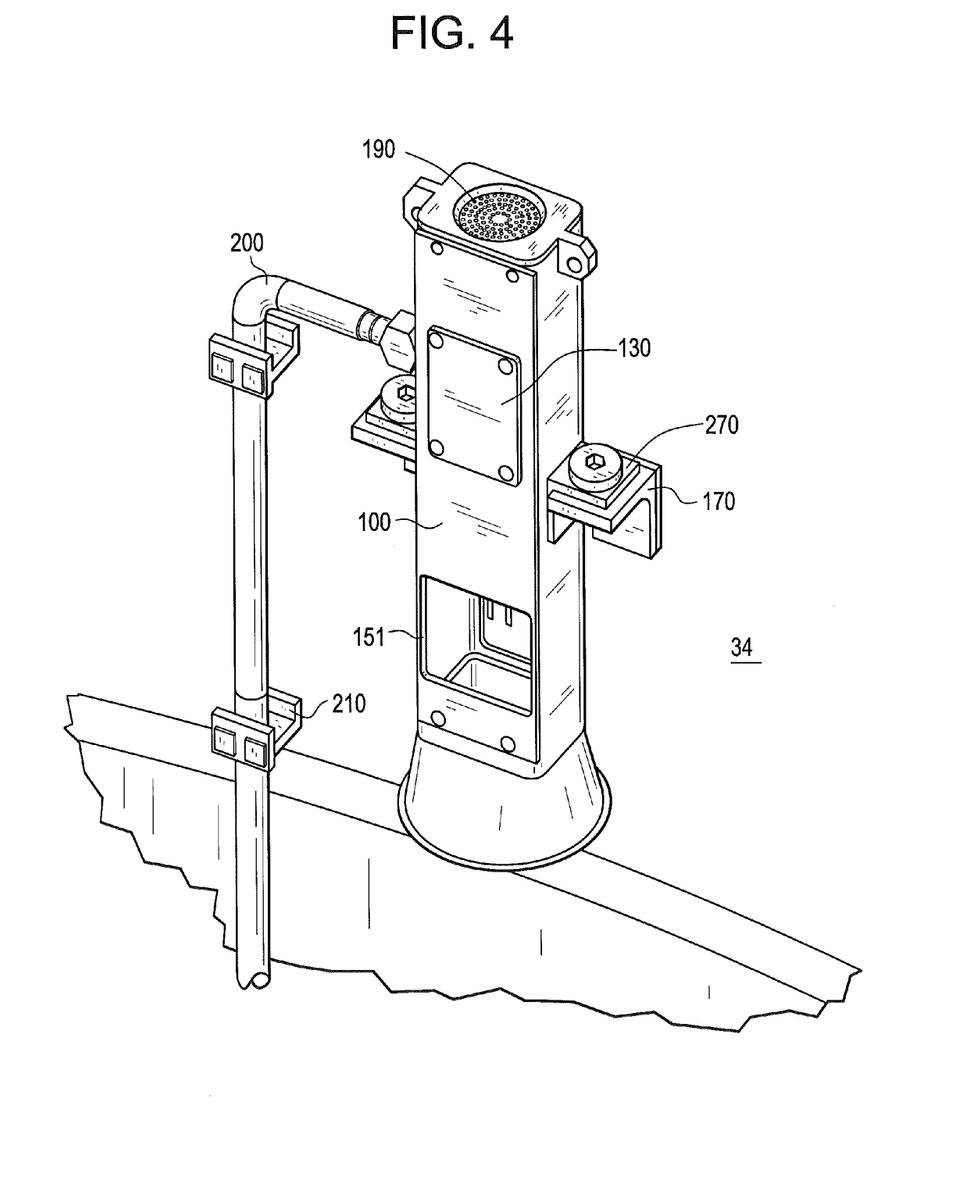
FIG. 4 is another illustration of an example embodiment ECP Probe Assembly installed in a nuclear reactor in example methods.

Structural body 110 may be generally enclosed to contain and force coolant fluid flow 160 through example embodiment ECP probe assembly 100 so as to maintain ECP probe 150 contact with active coolant for ECP monitoring. An exit filter 190, such as a screen mesh or perforated plate, may permit fluid coolant flow 160 to exit structural body 110 and capture any parts of ECP probe assembly 100 that may potentially detach into the coolant. A detection window 151 (FIG.

4) may be included in structural body 110 over ECP probes 150a, 150b, 150c, 150d, etc. Detection window 151 may be transparent to light or certain types of radiation, such that probes may detect radiation within the reactor, including alpha, beta, and electromagnetic radiation such as Cherenkov radiation. For example, detection window 151 may be an uncovered opening to permit maximum exposure.

Alternately, structural body 110 may include or form other holes or openings to adjust coolant flow, pressure, etc. as desired within structural body 110. Structural body 110 is shown with a generally rectangular cross-section and may, for example, have rectangular cross-section dimensions of about 4 inches by 3 inches. Of course, structural body 100 may have any shape or size that accommodates at least one ECP probe 150 and coolant flow 160, including cylindrical, square, conical, etc. Structural body shape and size may be varied to achieve a desired liquid coolant flow 160 rate or mass flow, to achieve a desired positioning within a subject reactor, and/or to achieve any other desired operational characteristic.

Example embodiment ECP probe assembly 100 further includes an inlet for fluid coolant flow 160 to flow within structural body 110 and exit 190. The inlet may include a venturi 120 that increases a speed of liquid coolant flow 160 through the example embodiment assembly 100 and/or collects liquid coolant flow 160 from a larger flow cross section in a reactor, to better estimate average coolant chemistry. Alternatively, other inlet structures, including diffusers, choke plates, filters, etc. may be used instead of, or in combination with, venturi 120 in example embodiment ECP probe assemblies to generate desired coolant flow and content. Venturi 120 or any other structure may be affixed to structural body 110 with fasteners 101 or any other joining mechanism, including welding or friction, for example.

As fluid coolant flows through example embodiment ECP probe assembly 100, one or more ECP probes 150 generate an electrical or other signal indicative of the ECP of a relevant material in the coolant flow. These signals may be transmitted through transmission media 141, which may include wires or other circuitry, for example. Transmission media 141 may also include wireless transmitters that transmit signals from ECP probes 150 through electromagnetic waves, for example, to an external receiver. Although ECP probes 150 may operate without external power, electrical or otherwise, transmission media 141 may supply power to any components of example embodiment ECP probe assembly 100. Transmission media may be communicatively connected to ECP probes 150 and exit assembly 100 through a communications port 140.

An access plate 130 may be removable from structural body 110 to provide specific access to a component inside example embodiment ECP probe assembly 100, particularly if the assembly 100 is installed in an area preventing removal or other access. Example embodiment ECP probe assembly 100 may further include one or more external securing structures such as mid-body extension(s) 170 and/or foot extension(s) 175. Extension 170 and/or 175 may permit joining, fastening, tying, etc. example embodiment ECP probe assembly 100 to an external component so as to rigidly secure assembly 100 in a particular vertical position within a reactor. For example, mid-body extensions 170 may accommodate a bolt therethrough to join assembly 100 to a flange. In this way, example embodiment ECP probe assembly 100 may be secured in a desired location to measure coolant ECP properties near a particular reactor component without repositioning or loss of coolant flow 160 during reactor operation. Of course, other joining/fixing devices and mechanisms are useable with example embodiment assemblies to ensure a desired positional characteristic.

The components described above, useable with example embodiment ECP probe assemblies, may be manufactured from materials designed to withstand operating conditions within a nuclear reactor. For example, any of venturi 120, structural body 110, alignment housing 155, and/or extension 175 and 170 may be fabricated from zircaloys, austenitic stainless steel, nickel alloys, etc. that substantially maintain their physical properties in high pressure/temperature aqueous environments with elevated levels and types of radioactivity. Or, for example, materials used in example embodiment ECP probe assemblies may be chosen to match materials to which the probe will be installed, so as to minimize material incompatibility and fouling.

Example embodiment ECP probe assemblies are thus useable in several harsh environments such as operating nuclear power reactors. It is understood that several features discussed above in connection with example embodiments may be reconfigured or omitted based on the specific application and/or desired operational characteristics of an ECP probe assembly. While example embodiment ECP probe assembly 100 may be installed and used in accordance with example methods discussed below, it is understood that other uses and installation locations may be applicable with example embodiment probe assemblies.

Example Methods

Figure 3:
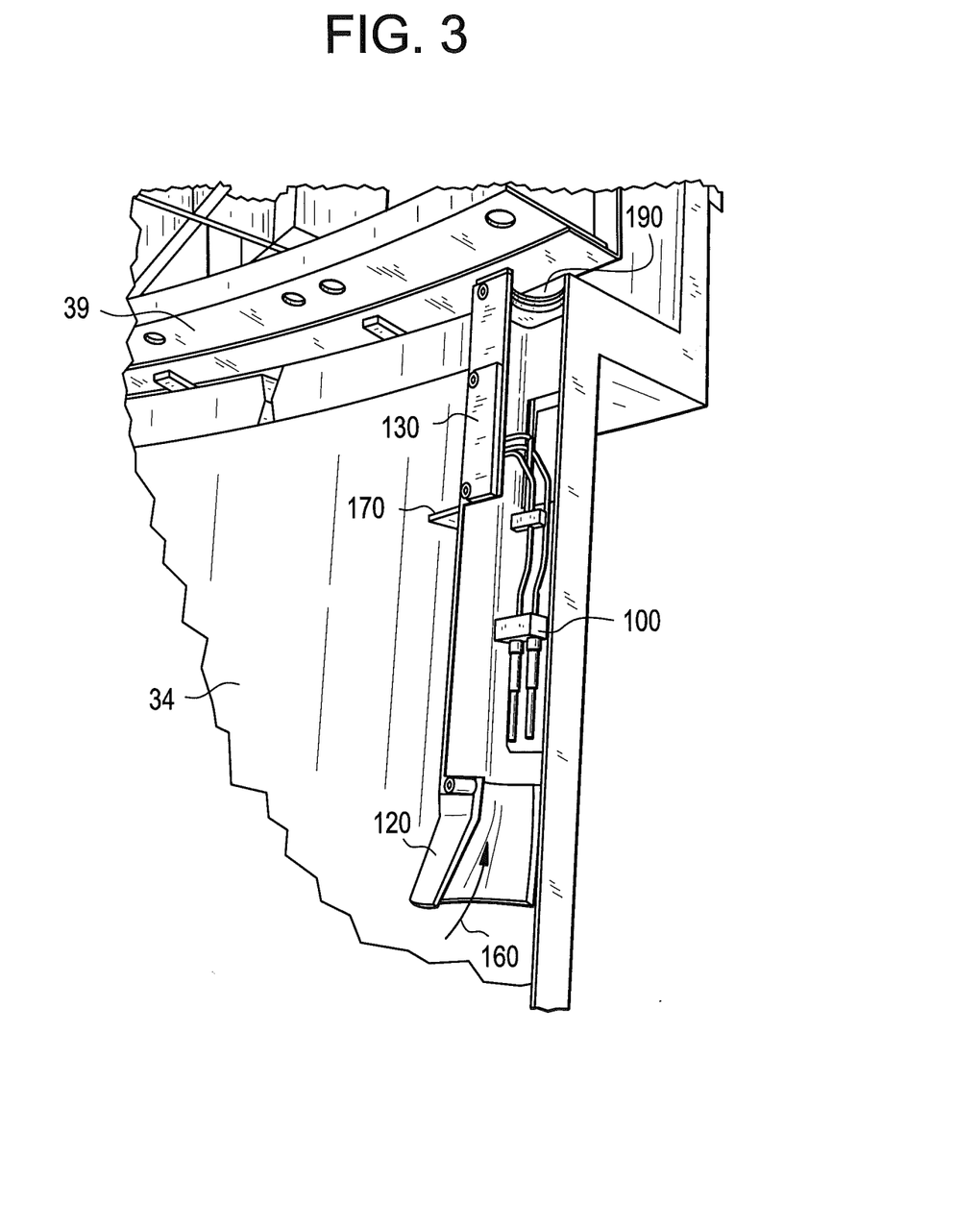
FIG. 3 is an illustration of an example embodiment ECP Probe Assembly installed in a nuclear reactor in example methods.

Example methods include installing an ECP probe assembly, such as example embodiment ECP probe assembly 100, in a nuclear reactor. Example methods include determining a location for installation of the ECP probe assembly within a nuclear power plant. Any location may be chosen that is in contact with coolant flowing in the operating reactor. The location does not depend on instrumentation tube access or other reactor vessel aperture access. For example, as shown in FIG. 3, a position about an inner circumferential surface of a core shroud 34, at a flange just below shroud head 39, may be a position of interest due to its proximity to welds within core shroud 34, elevated radiation levels experienced by these components and welds, and/or coolant chemistry at the position due to coolant possessing a high thermal energy after exiting core 36 (FIG. 1), just below the position. Because no or few vessel apertures or other access points may be near the position on core shroud 34, example embodiment ECP probe assemblies installed there may permit unique data gathering for improved plant operation and monitoring. As such a position, ECP probe assemblies may detect metal chemistry near a heat-affected zone of a major weld joint on the core shroud wall 34, and ECP probes 150a, 150b, 150c, and 150d may be aligned vertically within about 0.25 inch away from the detected metal surface so as to achieve accurate ECP measurement. Other positions within the nuclear plant and/or nuclear reactor may be chosen based on similar interests in material ECP properties in the coolant.

The ECP probe assembly may be installed in the desired position so as to receive and monitor material ECP properties at the position. The installation may occur during plant fabrication, during a fuel outage, or during any other periods when the location is accessible. The ECP probe assembly may be installed through several known methods of securely positioning components within a nuclear reactor. For example, ECP probe assembly 100 may be welded to a surface of core shroud 34 in FIG. 3. Or, as shown in FIG. 4, for example, foot extensions 175 (FIG. 2) may be bolted with lug bolts and/or pins 170 to a flange of core shroud 34 just below shroud head 39. Several alternate methods of installing and securing an ECP probe assembly at the desired position are possible, including use of fasteners, screws, tang/receptor matings, or mechanisms involving tying, friction, or adhesives.

Once installed at the desired position, power operations or other events within the nuclear reactor may be commenced that cause coolant flow 160 through ECP probe assembly 100. Although not necessary, ECP probe 100 may be installed with regard to known coolant flow 160 to permit fluid coolant to flow through ECP probe assembly 100 as it flows through the reactor vessel. For example, a clearance may be maintained about a coolant exit from ECP probe assembly 100 so as to ensure coolant flow 160 through the assembly. Coolant coming into contact with individual ECP probes within the ECP probe assembly 100 during operations may be monitored for material ECP properties. For example, ECP probes measuring ECP of stainless steel and zircaloys may come into contact with active coolant and detect stainless steel or zircaloy ECP from the coolant at the location of the ECP probe assembly 100. Through the ECP probe detection, material corrosion and potential cracking due to coolant effects near the location of ECP probe 100 for actual reactor materials may be accurately estimated.

ECP probes may transmit the data, including voltages reflecting corrosion, pH, other free ions, etc., directly to a user through transmitters in installed ECP probe assemblies, using electromagnetic signals detected by a user receiver outside the reactor, for example. If ECP probe assemblies installed in example methods require a hard-wired connection to transmit signals, a transmission conduit may further be installed in example methods. For example, as shown in FIG. 4, a transmission conduit 200 may be installed from a communications port 140, as shown in FIG. 2, in example embodiment ECP probe assembly 100 down the wall of core shroud 34 onto core plate 48. The transmission conduit 200 may be, for example, a radiation-hardened 1-inch or smaller pipe or tubing that insulates and separates transmission media 141, which may be a mineral-insulated wire within the tubing, carrying ECP data from ECP probes.

Transmission conduit 200 as shown in FIG. 4 may bend, change direction, or join to other features in order to provide a route for communications from ECP probe assembly 100. One or more braces 210 may secure and/or guide transmission conduit 200 against a core shroud 34 wall or other component, so as to prevent transmission conduit 200 loosening or vibration, for example.

Figure 5:
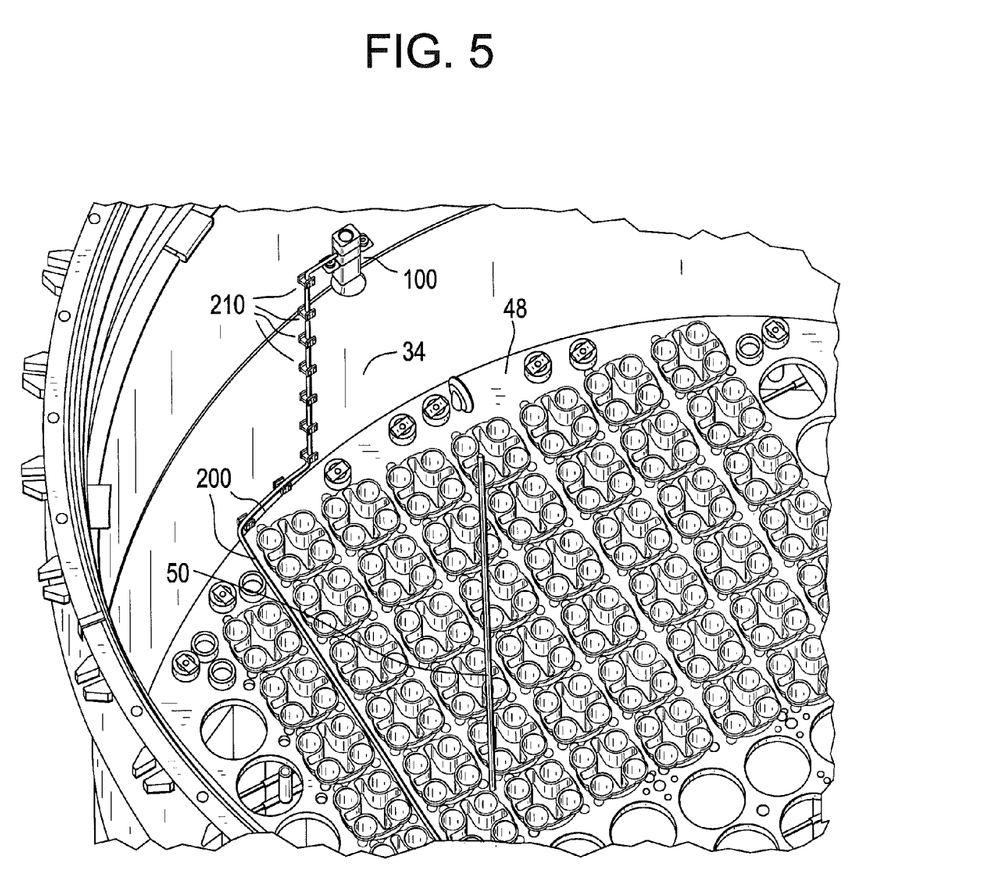
FIG. 5 is an illustration of a conduit routing from ECP probes to instrumentation tubes in a nuclear reactor in example methods.

As shown in FIG. 5, the transmission conduit 200 extend down a wall of core shroud 34 to core plate 48, where it bends or is otherwise routed onto core plate 48 to instrumentation tube 50 passing through core plate 48. In this routing, the transmission conduit 200 may have a minimal impact on coolant flow through a nuclear reactor and/or may not otherwise interfere with reactor operation. Transmission media 141 (FIG. 2) may run entirely through transmission conduit 200 without exposure to reactor coolant. Radiation and/or thermal shielding may be provided in transmission conduit 200 to minimize reactor operating conditions on transmission media 141. For example, as discussed above transmission media 141 may be a mineral insulated wire.

Figure 6:
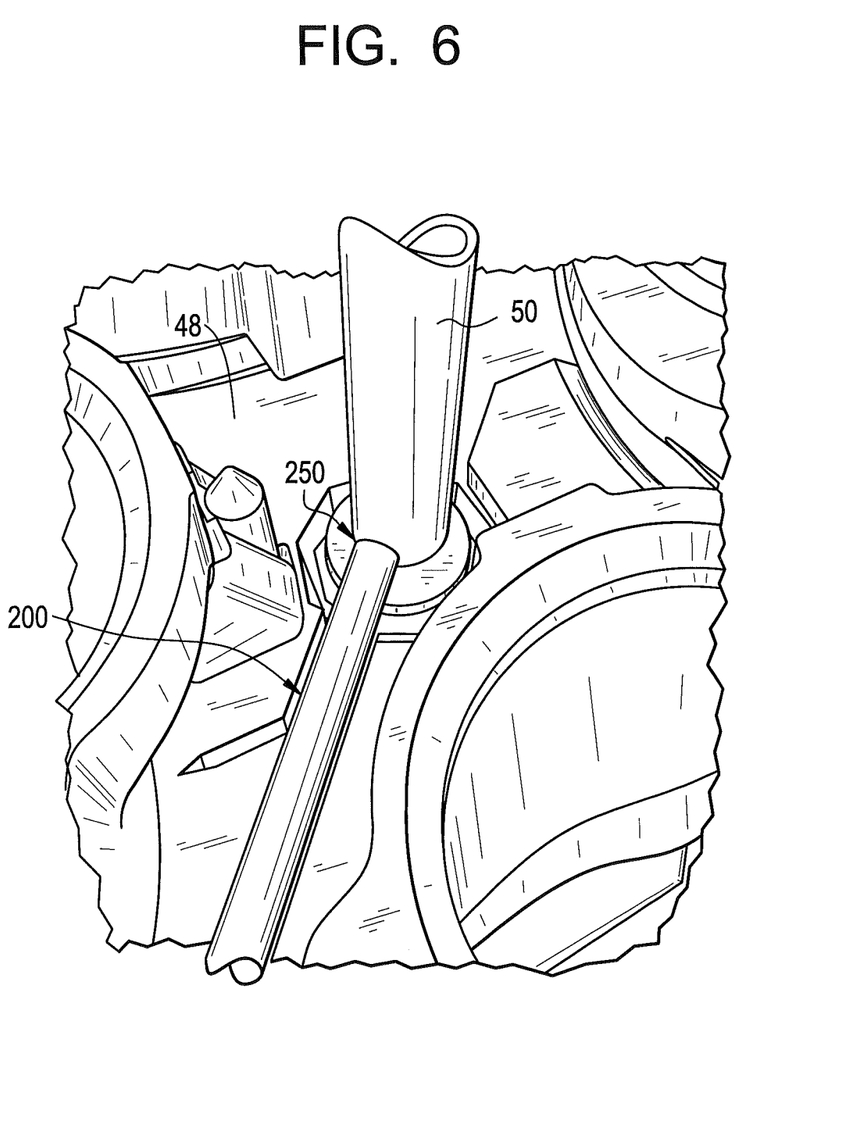
FIG. 6 is an illustration of a conduit joining instrumentation tubes in a nuclear reactor in example methods.

As shown in FIG. 6, where transmission conduit 200 joins to instrumentation tube 50, transmission media 141 may pass from transmission conduit 200 into instrumentation tube 50. The joining may be sealed, by welding 250 for example, to prevent coolant entry into instrumentation tube 50. Transmission media 141 may then be fed down instrumentation tube 50 outside of the reactor, communicatively connecting to conventional data acquisition system processing devices located in the drywell exterior to the reactor pressure vessel 12. Alternatively, transmission conduit 200 may join to any other aperture, used for instrumentation or otherwise, in a reactor vessel so as to feed data externally.

Upon installation of ECP probe assembly 100 and configuring and receiving data from the ECP probe assembly of material ECP at the installed position during reactor operation, plant operators may accurately assess coolant chemistry effects on plant components. Because example methods permit example embodiment ECP probe assemblies to be installed in several positions inaccessible during plant operation, and because example embodiment ECP probe assemblies may be configured with desired ECP probe types, ECP of a variety of different materials at several different positions with respect to several different components may be remotely assessed within an operating nuclear reactor. Plant operators may adjust plant chemistry components based on the data received from installed ECP probe assemblies during plant operation so as to improve component health, reduce component damage, etc.

Example embodiments and methods thus being described, it will be appreciated by one skilled in the art that example embodiments may be varied through routine experimentation and without further inventive activity. Variations are not to be regarded as departure from the spirit and scope of the example embodiments, and all such modifications as would be obvious to one skilled in the art are intended to be included within the scope of the following claims.

What is claimed is:

1. An electrochemical corrosion potential (ECP) probe assembly comprising:
   a plurality of ECP probes separate from each other within the ECP probe assembly useable in an operating nuclear reactor, the plurality of ECP probe each configured to detect ECP of different component materials when a fluid in the operating nuclear reactor contacts the plurality of ECP probes;
   a structural body housing the plurality of ECP probes and providing a fluid flow path so that the fluid flows through the assembly and contacts the plurality of ECP probes;
   at least one signal transmission medium configured to transmit the ECP for the different component materials from the plurality of ECP probes,
   wherein a first ECP probe of the plurality of ECP probes and a second ECP probe of the plurality of ECP probes are configured to detect the ECP for the different component materials and wherein the different component materials include stainless steel and a zirconium alloy.

2. The assembly of claim 1, wherein at least one of the first and the second ECP probes include platinum and iron ferrite sensors and detect ECP of the component material due to pH of the fluid.

3. The assembly of claim 1, wherein the structural body includes a single fluid inlet and a single fluid outlet so as to provide a single fluid flow path.

4. The assembly of claim 3, wherein the plurality of ECP probes are rigidly connected to the structural body so that the plurality of ECP probes are within the single fluid flow path.

5. The assembly of claim 3, wherein the structural body includes a venturi at the single fluid inlet and a screen mesh at the single fluid outlet.

6. The assembly of claim 1, further comprising:
   a communications port configured to communicatively connect the signal transmission medium to an external conduit, wherein the signal transmission medium is a conductive wire and the ECP of the fluid is transmitted as electrical signals on the conductive wire.

7. The assembly of claim 1, further comprising:
a plurality of extensions rigidly connected to the structural body, the plurality of extensions configured to secure the assembly to an external structure; and
a detection window permitting radiation incidence on the plurality of ECP probes.

8. The assembly of claim 1, wherein the stainless steel is an austenitic stainless steel.

9. A method of installing an electrochemical corrosion potential (ECP) probe assembly in a nuclear reactor, the method comprising:
securing an ECP probe assembly in a desired orientation and location inside of a reactor pressure vessel of the nuclear reactor, the ECP probe assembly including,
a plurality of ECP probes separate from each other within the ECP probe assembly and each configured to detect ECP of different component materials when a coolant in the nuclear reactor contacts the plurality of ECP probes,
a structural body housing the plurality of ECP probes and providing a coolant flow path so that the coolant flows through the assembly and contacts the plurality of ECP probes, and
at least one signal transmission medium configured to transmit the ECP of the coolant from the plurality of ECP probes; and
communicatively connecting the plurality of ECP probes to a receiver outside of the reactor pressure vessel,
wherein a first ECP probe of the plurality of ECP probes and a second ECP probe of the plurality of ECP probes are configured to detect the ECP for the different component materials, and wherein the different component materials include stainless steel and a zirconium alloy.

10. The method of claim 9, further comprising:
determining the desired location based on components in the reactor pressure vessel in proximity to the desired location, anticipated coolant conditions at the desired location, and anticipated radiation levels at the desired location.

11. The method of claim 9, wherein the desired location is on a core shroud wall at a top of the core in the reactor pressure vessel about a heat-affected zone of a major weld joint of the core shroud wall.

12. The method of claim 9, wherein the ECP probe assembly further includes a plurality of extensions rigidly connected to the structural body, and wherein the securing includes affixing the structural body to a reactor structure at the desired location via at least one of the extensions.

13. The method of claim 9, wherein the securing includes positioning the ECP probe assembly at an orientation with regard to anticipated coolant flow through the reactor pressure vessel so that the coolant flows through the ECP probe assembly in a same flow direction as through the reactor pressure vessel.

14. The method of claim 9, wherein the communicatively connecting includes connecting a communications conduit between the ECP and an instrumentation tube in the nuclear reactor, and wherein the communications conduit contains a transmission medium transmitting ECP data to the receiver outside the reactor pressure vessel.

15. The method of claim 9, wherein the desired location is on a core shroud wall at a top of the core in the reactor pressure vessel, and wherein the communications conduit runs down the core shroud wall to a core plate and across the core plate to the instrumentation tube.

16. The method of claim 9, wherein the stainless steel is an austenitic stainless steel.

17. A method of installing an electrochemical corrosion potential (ECF) probe assembly in a nuclear facility, the method comprising:
securing an ECP probe assembly in a desired location in the nuclear facility, the ECP probe assembly including,
a plurality of ECP probes separate from each other within the ECP probe assembly and each configured to detect ECP of different component materials when a fluid in the facility contacts the plurality of ECP probes,
a structural body housing the plurality of ECP probes and providing a fluid flow path so that the fluid flows through the assembly and contacts the plurality of ECP probes, and
at least one signal transmission medium configured to transmit the ECP of the fluid from the plurality of ECP probes; and
communicatively connecting the plurality of ECP probes to a receiver in a second location in the nuclear facility,
wherein a first ECP probe of the plurality of ECP probes and a second ECP probe of the plurality of ECP probes are configured to detect the ECP for the different component materials, and wherein the different component materials include stainless steel and a zirconium alloy.

18. The method of claim 17, wherein the stainless steel is an austenitic stainless steel.

19. The method of claim 17, wherein the ECP probe assembly further includes an extension rigidly connected to the structural body, and wherein the securing includes affixing the structural body to a structure at the desired location via the extension.

* * * * *